US006673835B1

(12) United States Patent
Hensley et al.

(10) Patent No.: US 6,673,835 B1
(45) Date of Patent: *Jan. 6, 2004

(54) METHOD AND COMPOSITION FOR DELIVERING ZINC TO THE NASAL MEMBRANE

(75) Inventors: Charles Hensley, Woodland Hills, CA (US); Robert Steven Davidson, Woodland Hills, CA (US)

(73) Assignee: Zicam LLC, Phoenix, AZ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/388,816

(22) Filed: Sep. 1, 1999

Related U.S. Application Data

(63) Continuation-in-part of application No. 09/603,864, filed on Jun. 26, 2000, now Pat. No. 6,365,624, and a continuation-in-part of application No. 09/145,042, and a continuation of application No. 09/145,042, filed on Sep. 1, 1998, now Pat. No. 6,080,783.

(51) Int. Cl.⁷ .......................... A01N 25/04; A61K 9/10; A61K 31/315; A61K 33/30

(52) U.S. Cl. ...................... 514/494; 514/772; 514/777; 514/778; 514/779; 514/780; 514/781; 514/782; 514/783; 514/944; 514/946; 514/964; 514/975; 424/400; 424/484; 424/485; 424/488; 424/641; 424/643

(58) Field of Search .............................. 424/400, 641, 424/643, 484, 485, 488; 514/494, 944, 946, 772, 777–783, 975

(56) References Cited

U.S. PATENT DOCUMENTS

| 4,724,231 | A | * | 2/1988 | Wenig ........................ 514/52 |
| 4,885,287 | A | | 12/1989 | Hussain et al. ............. 514/159 |
| 5,208,031 | A | | 5/1993 | Kelly ........................ 424/401 |
| 6,080,783 | A | * | 6/2000 | Davidson et al. ........... 514/494 |
| 6,365,624 | B1 | * | 4/2002 | Davidson et al. ........... 514/494 |

OTHER PUBLICATIONS

CRC Handbook of Chemistry and Physics, CRC Press, Inc., Florida, 59th ed., p. F–55, 1979.*

* cited by examiner

Primary Examiner—John Pak
(74) Attorney, Agent, or Firm—Snell & Wilmer L.L.P.

(57) ABSTRACT

A viscous gel for delivering minor effective amounts of active substances through the nasal membrane into the body.

6 Claims, No Drawings

METHOD AND COMPOSITION FOR DELIVERING ZINC TO THE NASAL MEMBRANE

CROSS REFERENCE TO RELATED APPLICATIONS

This application is a continuation-in-part of application Ser. No. 09/145,042, filed Sep. 1, 1998, which issued as U.S. Pat. No. 6,080,783, and of application Ser. No. 09/603,864, filed Jun. 26, 2000, which issued as U.S. Pat. No. 6,365,624, which is a continuation of application Ser. No. 09/145,042, filed on Sep. 1, 1998, now U.S. Pat. No. 6,080,783.

This invention relates to compositions and methods for delivering minor effective amounts of a substance to the blood in a body.

More particularly, the invention relates to a method and composition for delivering a minor effective amount of a substance to the nasal membrane.

In a further respect, the invention relates to a composition which maintains zinc in an ionic state for delivery to the nasal membrane.

In another respect, the invention relates to a composition which maintains a substance in direct contact with the nasal membrane for an extended period of time.

The common cold is one of the most frequently occurring human illnesses and is responsible for substantial morbidity and economic loss. Ionic zinc is a known effective anti-rhinovirus agent in vitro and in vivo.

In one in vivo study reported in 1991, a double-blind clinical trial demonstrated the effectiveness of orally administered zinc gluconate/glycerine lozenges. The lozenges used in the study contained twenty-three milligrams of zinc provided by 179 milligrams of zinc gluconate trihydrate which provided a 13.1 millimolar ionic zinc concentration in the oral cavity. During the study, lozenges administered at two hour intervals resulted in a forty-two percent reduction in mean cold duration and in a marked reduction in both the number and severity of symptoms if treatment with the lozenges was initiated within two days of the onset of cold symptoms. A second study reported in 1992 (Zarmebo J. E., Godfrey J. C., Godfrey N., *J Pharm Sci* 1992; 81: 128–130) confirmed the findings of the 1991 study. Soon after the results of these studies became widely known, a number of companies began marketing their own versions of the zinc lozenge cold remedy.

While zinc lozenges are usually beneficial in treating a cold, the lozenges have several drawbacks. First, the majority of zinc in a zinc gluconate lozenge is released in the oral cavity. The principal site, however, of antiviral activity is believed to be the nasal cavity (Novick S. G., Godfrey J. C., Godfrey N. J., Wilder H. R., *Medical Hypothesis* 1996; 46: 295–302). It is surmised that some ionic zinc released by a lozenge in the oral cavity makes its way to nasal passages where the zinc binds to viral ICAM-1 receptors and inhibits rhinovirus from binding to and infecting nasal mucosal cells. The difficulty encountered by ionic zinc or another substance in a lozenge in attempting to travel from the oral cavity to the nasal cavity limits the effectiveness of lozenges. Further, in a congested individual the route from the oral cavity to the nasal cavity may be completely blocked, rendering the lozenges ineffective.

A second disadvantage associated with zinc lozenges is the production of significant side effects. In one study, twenty percent of the subjects complained of nausea and eight percent complained of bad taste reactions (Novick S. G., Godfrey J. C., Godfrey N. J., Wilder H. R., *Medical Hypothesis* 1996; 46: 295–302). With respect to the nausea, it is well established that excessive zinc in the intestinal tract interferes with copper absorption and that preventing the absorption by the body of sufficient quantities of copper can lead to a variety of undesirable pathological states. The overuse of zinc lozenges may contribute to copper depletion.

We have discovered a novel gel composition and method for delivering ionic (negatively charged) zinc and other active substances to the nasal epithelial membrane without encountering the disadvantages normally associated with lozenges. The composition maintains ionic zinc or another active substance in direct contact with the nasal membrane, preferably for an extended period of time of at least one-quarter hour, and delivers zinc or another active substance into the nasal membrane and into blood in the nasal membrane.

When the gel composition is a homeopathic composition, it includes from 75% to 99.999% by weight of at least one carrier and a minor effective amount of an active substance. The minor effective amount in the gel composition includes from 0.0000001% to 5.0% by weight of the active substance.

When the gel composition is a pharmaceutical composition, it includes from 75% to 99.999% by weight of at least one carrier and a minor effective amount of an active substance. The minor effective amount includes from 0.0000001% to 10.0% by weight in the composition of the active substance. As would be appreciated by those of skill in the art, small concentrations of active substances may not be deemed homeopathic but can still be beneficial to the body. Such "non-homeopathic" concentrations of an acitve substance are herein deemed to produce a pharmaceutical composition.

When the gel composition is a homeopathic composition and zinc is the active substance, the composition includes from 0.185% to 2.8% by weight (from about 4 mM to 60 mM), preferably 0.9% to 2.0% by weight (from about 20 mM to 44 mM), zinc gluconate. Each 0.1% by weight zinc gluconate in the composition produces a concentration of approximately 0.014% by weight ionic zinc (i.e., of about 2.2 mM ionic zinc). At least a 4 mM concentration of ionic zinc is preferred in the gel composition to insure that a sufficiently high concentration of ionic zinc is produced by the composition at the interface between the composition and the nasal membrane.

The composition has a viscosity in the range of 2,500 to 40,000 centipoise, preferably 5,000 to 20,000 centipoise. The viscosity of the composition is important because it facilitates maintenance of the composition in the nasal cavity in contact with the nasal membrane or with mucous on the membrane. When the viscosity is less than about 2,500 centipoise, the composition tends to be drawn by gravity out of the nasal cavity. If the viscosity is in excess of about 40,000 centipoise, the thickness of the composition interferes with the diffusion of ionic zinc through the composition to the nasal membrane. During the development of the composition of the invention, nasal sprays were considered and discarded because the low viscosity of the liquids comprising such sprays allows the liquids to flow under gravity out of the nasal cavity, preventing the sprays from contacting the nasal membrane for an extended period of time. The effectiveness of a nasal spray usually substantially dissipates in less than five minutes. Similarly, applying the composition on a swab or nose plug is not believed efficient because the swab or nose plug, which may for example be made of cotton or of a sponge material retain the composition and interferes with the delivery of an additional supply of the composition into contact with the nasal membrane following dissipation of the composition which is on the surface of the swab or plug and is in direct contact with the nasal membrane.

As noted, nasal sprays were avoided during development of the invention. By way of background with respect to zinc—bearing nasal sprays, U.S. Pat. No. 5,688,32 concerns antiallergic spray preparations and discloses and claims a method for the treatment of an allergic condition in which a spray solution is applied to the eye or respiratory tract of a mammal having the allergic condition. The spray solution includes a non-toxic, anti-allergy effective amount of ionic zinc in a concentration below that which causes irritation to mucus membranes. The majority of the ionic zinc in the spray solution is unchelated zinc and is in the form of free ionic solution, wherein the solution has a zinc ion content of between about 0.002 and about 0.12%(w/v). The allergic condition treated with the spray solution can comprises hay-fever and asthma. The spray solution can be selected from the group consisting of essentially aqueous and essentially saline solutions; can have a zinc ion content of about 0.04% (w/v); can comprise a mineral acid salt of zinc as solute; can comprise a solute selected from the group consisting of zinc sulfate and zinc chloride; can be dispensed in aliquots of about either 0.05 to 0.5 ml or 0.2 ml; and/or, can include at least one other pharmaceutically acceptable ingredient. The other pharmaceutically acceptable ingredient can be selected from the group consisting of antihistamines, scenting agents and active ingredients; or, can comprise ascorbate. U.S. Pat. No. 5,688,532 also discloses and claims an improvement in a method for treatment of an allergic condition by the administration of a zinc compound to a mammal possessed of an allergic condition. The improvement consists essentially of spraying a solution comprising a non-toxic, anti-allergy effective amount of ionic zinc to the eye or respiratory tract of a mammal possess of the allergic condition. The solution comprises a concentration of ionic zinc below that which causes irritation to mucus membranes. The majority of the ionic zinc in the spray is unchelated zinc and is in the form of free ionic solution. The solution has a zinc ion content of between about 0.002 and 0.12%(w/v).

U.S. Pat. No. 5,622,724 discloses and claims a method for the treatment of the symptoms of the common cold comprising administering a spray of a solution containing a non-toxic, symptom effective treating amount of a solution of a substantially unchelated ionic zinc compound. The solution contains substantially unchelated zinc ions in a concentration of from about 0.004 to about 0.12% (w/vol), to the nostrils and respiratory tract of a patient in need thereof. The solution can be selected from the group consisting of aqueous and saline solutions; can further comprises an effective amount of a flavor and/or odor enhancing agent; can have an unchelated zinc ion content of about 0.04% (w/v); or, can consist essentially of the substantially unchelated ionic zinc compound and at least one pharmaceutically acceptable carrier. The substantially unchelated ionic zinc compound can comprise a mineral acid salt of zinc; can comprise a salt selected from the group consisting of zinc sulfate and zinc chloride; or, can comprise zinc sulfate. Utilization of zinc chloride at concentrations greater than 0.2%, especially greater than 0.4% is not preferred because, as is well known in the art, the zinc chloride is caustic. The carrier utilized in the invention can include 0.05% to 5.0% by weight glycerine. The glycerine is important and is presently preferred because it allows zinc to remain in an ionic state until the zinc contacts the nasal membrane and/or mucous on the nasal membrane. One problem encountered during development of the invention was identifying a carrier which maintains zinc in an ionic state.

The gel composition of the invention which utilizes zinc as the active substance preferably permits ionic zinc to diffuse through the composition to the nasal epithelial membrane or mucous on the epithelial membrane. This facilitates the availability of a continuous supply of ionic zinc because the composition will continue via diffusion to supply zinc without requiring that the portion of the composition adjacent the nasal epithelial membrane (on mucous on the membrane) dissolve or dissipate and expose a fresh portion of the composition containing ionic zinc. As noted, composition viscosities in excess of about 40,000 centipoise are believed to interfere with the diffusion of zinc through the composition. Viscosity measurements recited herein were obtained using the Brookfield Syncho-Lectric Viscometer for the measurement of the apparent Viscosity of Newtonian and Non-Newtonian materials at low shear rates at given rotational speeds (ASTM D1824-87). See also ASTM D1084-88, ASTM D2196-86 and other ASTM protocols concerning the measurement of viscosity.

We have also discovered a method of delivering minor effective amounts of a metal into the blood. The metal is the active substance. The method includes the step of providing a viscous delivery composition. The delivery composition includes 90% to 99.995% by weight of at least one carrier and less than 1.5% by weight of the metal. The composition has a viscosity in the range of 2,500 to 40,000 centipoise. The method includes the additional steps of applying the delivery composition in the nasal cavity in direct contact with the nasal membrane, and maintaining the delivery composition in contact with the nasal membrane for at least one-sixth hour.

In another embodiment of the invention, we provide an improved method of delivering minor effective amounts of an active substance into the blood. The method includes the step of providing a viscous delivery composition including 75% to 99.999% by weight of at least one carrier, and a minor effective amount of the active substance. The composition has a viscosity in the range of 2,500 to 40,000 centipoise. The method also includes the step of applying the delivery composition in the nasal cavity. The nasal cavity includes mucous, cilia and a nasal membrane. The delivery composition is applied such that a first portion of the composition directly contacts at least the nasal membrane, a second portion of the composition directly contacts at least mucous in the nasal cavity, and at least a third portion of the composition directly contacts at least cilia in the nasal cavity. The method also includes the step of maintaining the first portion of the delivery composition in contact with the nasal membrane for at least ten minutes.

In a further embodiment of the invention, we provide an improved method of delivering a minor effective amount of an active substance to the blood and of reducing the time required to deliver the substance into the blood by increasing the ability of the active substance to penetrate the body. The improved method comprises the steps of providing at least one carrier; providing at least one active substance; and, providing at least one permeation enhancer to facilitate passage of the active substance through a nasal membrane in a nasal cavity. The nasal cavity also includes mucous and cilia. The improved method further includes the step of combining the carrier, active substance, and permeation enhancer to produce a viscous delivery composition including 75% to 99.999% by weight of said carrier, including a minor effective amount of the active substance, and including a minor effect amount of the permeation enhancer. The composition has a viscosity in the range of 2,500 to 40,000 centipoise. The method also includes the step of applying the delivery composition in the nasal cavity such that a first portion of the composition directly contacts at least the nasal membrane, such that a second portion of the composition directly contacts at least the mucous in the nasal cavity, and at least a third portion of the composition directly contacts the cilia in the nasal cavity; and, maintaining the first portion of said delivery composition in contact with the nasal membrane for at least ten minutes.

In still another embodiment of our invention, we provide an improved method of delivering a minor effective amount of an active substance to the blood and of reducing the time required for the active substance to pass through membrane into the blood by increasing the surface area over which the active substance contacts the body. The improved method includes the step of providing a viscous delivery composition including 75% to 99.999% by weight of at least one carrier, and a minor effective amount of the active substance. The composition has a viscosity in the range of 2,500 to 40,000 centipoise. The method also includes the step of applying the delivery composition in the nasal cavity. The nasal cavity includes a nasal membrane, cilia and mucous. A first portion of the composition directly contacts at least the nasal membrane, a second portion of the composition directly contacts at least said mucous in the nasal cavity, and at least a third portion of the composition directly contacts at least the cilia in the nasal cavity. The improved method also includes the step of increasing the action of the cilia in the nasal cavity.

In yet a further embodiment of our invention, we provide an improved method for controlling the rate at which minor effective amounts of an active substance are delivered into the blood. The improved method includes the step of providing a viscous delivery composition including 75% to 99.999% by weight of at least one carrier, and a minor effective amount of the active substance. The composition has a viscosity in the range of 2,500 to 40,000 centipoise. The method also includes the steps of determining the carrier diffusion rate at which the active substance diffuses through the carrier at a selected temperature and a selected pressure; determining the membrane diffusion rate at which the active substance penetrates a nasal membrane when the delivery composition contacts the nasal membrane at the selected temperature and pressure; selecting at least one of a diffusion rate pair comprising the carrier diffusion rate, and the membrane diffusion rate;and, adding a component to the viscous delivery composition to produce a modified viscous delivery composition in which the diffusion rate of the one of the diffusion rate pair is altered.

The following examples depict the presently preferred embodiments of the invention for the purposes of illustrating the practice thereof and not be way of limitation of the scope of the invention. In the examples, all proportions are by weight, unless otherwise noted.

EXAMPLE 1

One liter of a gel composition is prepared by mixing together purified water, glycerin, carbopol, and zinc gluconate. The gel includes:

| Component | Weight Percent | |
|---|---|---|
| PURIFIED WATER | 97.0 | |
| GLYCERIN U.S.P. | 2.0 | |
| CARBOPOL 940 nf | 0.5 | |
| ZINC GLUCONATE (source of ionic zinc) | 1.5 | (33.3 millimolar concentration) * |

* The molecular weight of zinc gluconate, about 450 g/mole, multiplied times 0.0333 moles per liter of zinc gluconate gives a weight of about 15 grams per liter of the gel composition.

The concentration of zinc gluconate in the gel composition of the invention is preferably in the range of from 0.185% to 2.8% by weight (from about 4 mM to 60 mM), preferably 0.9% to 2.0% by weight (from about 20 mM to 44 mM), zinc gluconate. The carrier in the gel composition can vary as desired, but presently preferably includes 90.0 to 99.0% purified water, 0.05 to 5.0% by weight glycerine (a thickener which also functions to permit zinc to maintain its ionic state), and 0.000001% to 5.0% by weight, preferably 0.1% to 3.0% by weight, of a carbohydrate or other thickener. A carbohydrate thickener is presently preferred. Other thickeners which can be utilized include: carrageenan, sugar, guar gum, and methylcellulose. The glycerine in the carrier produces a matrix which permits zinc ions to readily diffuse therethrough. The glycerine is also preferred because it has the ability to dissolve into and permeate mucous and the nasal epithelial membrane, carrying with it ionic zinc.

EXAMPLE 2

Two hundred and fifty microliters of the zinc gel of Example 1 is placed in one nasal passage of a healthy thirty-nine year old male Caucasian patient. Two hundred and fifty microliters of the zinc gel of Example 1 is then placed in the other nasal passage of the patient. Consequently, a total of 500 microliters of the gel is placed in the patient's nose. A first portion of the gel contacts at least a portion of the nasal epithelial membrane. A second portion of the gel contacts at least a portion of the mucous in the patient's nose. A third portion of the gel contacts at least cilia in the patient's nose. The gel remains in contact with at least a portion of the nasal epithelial membrane, the cilia, or mucous on the membrane. After four hours the zinc gel has completely dissipated.

EXAMPLE 3

Example 2 is repeated, except the individual is a twenty-four year old African American patient who has been experiencing mild cold symptoms for one day. The gel remains in contact with at least a portion of the nasal epithelial membrane or the mucous layer on the membrane. After four hours the zinc gel has completely dissipated and the patient notices a marked reduction in the severity of his cold symptoms.

EXAMPLE 4

Example 3 is repeated, except that the zinc gel of the invention is not administered to the twenty-four year old African American patient, nor is any other medication. After four hours, he does not notice any reduction in the severity of his cold symptoms.

EXAMPLE 5

Examples 3 and 4 are repeated, except the individual treated is a fifteen year old Japanese girl who has been suffering from mild cold symptoms for a day. Similar results are obtained.

EXAMPLE 6

Examples 3 and 4 are repeated, except the individual treated is a fifty year old Caucasian man who has been suffering from cold symptoms for two days. Similar results are obtained.

EXAMPLE 7

Example 2 is repeated except that the concentration of zinc in the nasal mucosa is measured just prior to insertion of the zinc gel; and, is measured ten minutes, thirty minutes, one hour, two hours, three hours, and four hours after the gel is inserted in the individual's nasal cavity. The following results are obtained:

| Time of Measurement | Zinc Concentration (Wt. %) |
| --- | --- |
| Just prior to administration of zinc gel | 0.003% |
| Ten minutes after administration of zinc gel | 0.008% |
| One-half hour after administration of zinc gel | 0.01% |
| One hour after administration of zinc gel | 0.01% |
| Two hours after administration of zinc gel | 0.011% |
| Three hours after administration of zinc gel | 0.012% |
| Four hours after administration of zinc gel | 0.012% |

EXAMPLE 8

Examples 1 to 6 are repeated, except that the concentration of ionic zinc in the composition is 20 mM instead of 33.3 millimolar. Similar results are obtained.

EXAMPLE 9

Example 1 to 6 are repeated, except that the concentration of ionic zinc in the composition is 44 mM instead of 33.3 millimolar. Similar results are obtained.

EXAMPLE 10

Examples 1 to 6 are repeated, except that the concentration of ionic zinc in the composition is 10 mM instead of 33.3 millimolar. Similar results are obtained.

EXAMPLE 11

Example 1 is repeated, except that the zinc gel composition is prepared utilizing 1.5% by weight of NATROSOL (TM) (hydroxyethylcellulose) in place of carbopol and 96% by weight purified water instead of 97% by weight purified water. The weight percent of each of the glycerin and zinc gluconate in the gel composition is unchanged.

EXAMPLE 12

Examples 2 to 7 are repeated, except that the zinc gel composition of Example 11 is utilized in place of the zinc gel composition of Example 1. Similar results are obtained.

EXAMPLE 13

Examples 8 to 10 are repeated except that the zinc gel composition of Example 11 is utilized in place of the zinc gel composition of Example 1, and the ionic zinc concentration in the Example 11 zinc gel composition is altered as specified in each of Examples 8 to 10. Similar results are obtained.

The NATROSOL utilized in Example 11 is obtained from Hercules Coporation of 1313 North Market Street, Wilimington, Del. 19894. Hydroxyethylcellulose can be obtained from other vendors.

One of the objectives of the invention is the delivery into the blood via the nasal membrane homeopathic concentrations of metals, chemical elements or other active substances. This ordinarily requires the delivery of specific selected titrated concentrations (i.e., minor effective amounts) of a substance. If an active substance or component is delivered to the blood stream in a concentration which is too high, this can have an adverse effect in the body. The delivery of minor effective amounts of active substances to the blood stream via the nasal membrane in accordance with the invention is believed highly advantageous because it offers a rapid delivery into the blood stream of selected metered minor effective amounts of a metal, chemical element(s), composition(s), or other active substance. Attempting to deliver orally homeopathic titrated amounts of chemical elements or compositions often is not believed practical because of the degradation of chemical elements which occurs in the oral cavity. As earlier noted, as used herein homeopathic concentrations of an active substance in the gel composition of the invention occur when the active substance is in the gel composition in a minor effective amount at a concentration in the range of 0.0000001% to 5.0%.

As utilized herein, a metal, chemical element, or other component or chemical composition is deemed an active substance if the metal, chemical element, etc. produces a beneficial physiological effect on the body. An active substance produces a beneficial physiological effect on the body if the substance after entering a patient's body the active substance benefits the skeletal system, the digestive system, the respiratory system, the circulatory system, the reproductive system, the urinary system, the endocrine system, the skin, or the nervous system of the body. One way an active substance can produce a beneficial physiological effect is by helping the body fight disease. Another way is by helping the body heal. Another way by improving the functioning of a system in the body. As would be appreciated by those of skill in the art, an active substance can comprise any of a large list of chemical compositions including, but not limited to vitamins, minerals, insulin and other polypeptides, nicotine, genes, substances which alter genes or which facilitate the formation of genes or which disable genes, and pharmaceutical and homeopathic substances. Nicotine can function as an active substance when used to compensate for the nicotine in cigarettes in order to facilitate a person in breaking the habit of smoking cigarettes. This benefits the lungs and other systems and organs in the body.

As used herein, the carrier comprises all the components in the nasal gel composition other than the active substance (s) in the nasal gel. Consequently, the carrier includes the fluid component of the gel composition (i.e., water, oil, alcohol, etc.), includes any thickeners in the nasal gel (i.e., glycerin, carrageenan, sugar, guar gum, methylcellulose, etc.), includes permeation enhancers (i.e., liposomes, chitosan, cyclodextrin, etc.), and includes any other components besides active substances.

As used herein, a permeation enhancer functions to facilitate the passage of an active substance through the nasal membrane, to protect an active substance from being damaged or altered as it passes through the nasal membrane, and/or to carry an active substance to a desired target in the body after the active substances passes through the nasal membrane. Examples of membrane permeation enhancers include liposomes, chitosan, and cyclodextrin. A liposome can encapsulate a drug or other active substance and can protect the drug from damage or alteration when the liposome passes through the nasal epithelial membrane. The liposome may also facilitate passage through the nasal epithelial membrane by entering, passing through, and exiting a cell which comprises a portion of the nasal membrane. A liposome can be constructed to be a "stealth" liposome which can not be "seen" by the liver and degraded by the liver. For example, putting polyethylene glycol in a small concentration in a liposome turns the liposome into a "stealth" liposome which is not "seen" and degraded by the liver. The liposome may also be targeted to a specific site in the body. For example, an antigen can be removed from cardiac tissue and used to make an antibody. The antibody is placed in the liposome carrying the active substance. When the liposome passes through the nasal membrane and enters the body, the antibody will—along with the liposome and active substance carried in the liposome—seek out an antigen on the heart corresponding to the kind of antigen used to produce the antibody. Protease inhibitor might function as a permeation enhancer by altering the physical characteristics of a liposome or of the nasal membrane in order to facilitate the passage of an active substance through the nasal membrane. Permeation enhancers are present in the nasal gel in a concentration in the range of 0.000001% to 5.0%.

As used herein, the matrix includes the liquid (i.e., water, oil, alcohol, etc.) and the thickener (carrageenan, sugar, guar gum, etc.)

Zinc in the nasal cavity acts as a decongestant, enhancing the discharge of mucous and inhibiting the generation of new mucous. Menthol is also a decongestant and can be incorporated in the composition of the invention in a concentration of 0.000001% to 0.10% by weight. Menthol is a bronchial dilator, functioning to open air passages in the lungs and to help discharge mucous.

When the zinc gel of the invention is applied to the nasal cavity, zinc ions diffuse from the gel matrix into the mucous or mucous membrane in the nasal cavity. It is believed that the zinc concentration in the mucous or mucous membrane creates a barrier which inhibits viral infection of the nasal epithelial membrane. As ionic zinc is absorbed from the gel into the mucous membrane and other nasal epithelial cells, the gel matrix permits new zinc to diffuse into the nasal membrane. The gel matrix has micelle cell—like properties which facilitate the diffusion of zinc through the gel matrix.

The homeopathic concentration of zinc ions in the zinc gel of the invention is 4 millimolar (mM) to 60 millimolar, preferably 20 mM to 44 mM. Concentrations of zinc in excess of 44 mM are not preferred unless an antioxidant or other component is included in the gel composition to protect the nasal epithelial membrane from abnormally high concentrations of zinc. Examples of antioxidants include ascorbic acid and SOD. The concentration of an antioxidant in the gel composition of the invention is in the range of 0.000001% to 5.0%.

The liquid component(s) in the carrier can be water, an oil(s), and/or an alcohol(s). The liquid component can from from 0% to 100% water, from 0% to 100% oil, or from 0% to 100% alcohol. Examples of oils are polyunsaturated oils, monosaturated oils like omega 3 and omega 6, and DHA. An example of an alcohol is ethanol.

Utilizing a oil, either alone or in combination with water and/or alcohol, can be desirable when the active substance is fat soluble. An example of a fat soluble active is vitamin A. Fat soluble actives typically are included in the nasal gel composition of the invention in a concentration in the range of 0.000001% to 4% weight percent.

Emulsifiers can be included in the nasal gel composition of the invention, especially when the carrier includes water and oil. Glycerol is an example of an emulsifier because it helps to combine oil with water and to protect the membrane by moisturizing it. The concentration of emulsifiers in the nasal gel composition is presently preferably in the range of 0.000001% to 5.0%.

Proteins, polypeptides, nucleic acids, and amino acids are additional examples of potential active substances for the nasal gel composition of the invention. A polypeptide is not a protein but is a polyamide that is obtained by the partial hydrolysis of proteins or by synthesis. A polypeptide yeilds amino acids on hydrolysis but has a lower molecular weight than a protein. The nasal membrane does not, in general, like proteins and tends to prevent proteins and polypeptides, even the smallest polypeptides, from passing into and through the nasal membrane. The nasal membrane can also tend to prevent the passage of amino acids; however, in some cases the nasal membrane does not prevent the passage of amino acids because there are transporters in the nasal membrane for certain amino acids. Often times enzymes are polypeptides. Hormones like insulin, growth hormones, and secretin are polypeptides. Insulin is a polypeptide.

Enzymes like protease inhibitors can function as permeation enhancers because they facilitate passage of the actives through the nasal membrane.

Hydroxycellulose or other thickeners or components can, if desired, be utilized to form colloidal solutions (i.e., suspensions) in order to increase the viscosity of the carrier in the nasal gel composition. The presently preferred concentration for thickeners is 0.000001% to 5.0% by weight.

Permeation enhancers can, by enlarging or loosening tight junctions between cells in the nasal membrane, facilitate the passage of an active substance, of a liposome, or of another permeation enhancer through the nasal membrane. By way of example, and not limitation, EDTA can chelate calcium. By taking calcium out of the cell junctions, EDTA may loosen up the junctions to facilitate passage of an active substance, liposome, etc. through the junction. Liquid permeation enhancers include ascorbic acid in water, glycerol in water, chitosan in water, and lysophosphotidylcholin in oil. The concentration of permeation enhancers in the nasal gel is in the range of 0.00001% to 5.0%

Other antioxidants which can be utilized in the gel of the invention include green tea catechin, epigallate, and selenium. The presently preferred concentration range for an antioxidant in the gel composition is from 0.000001% to 5.0%.

Varying the rate of diffusion of an active substance through the carrier, the nasal epithelial mucous membrane, or through mucous in the nose is important in the practice of the invention.

In order to increase the rate of diffusion of an active substance through the nasal membrane, the concentration of a permeation enhancer like vitamin C or a liposome can be increased. Permeations enhancers like vitamin C or liposomes can be included in the nasal gel at concentrations in the range of 0.000001% to 5.0% by weight. Making the nasal gel less viscous is another way of increasing the diffusion of an active substance through the nasal membrane. Normally an active substance or a permeation enhancer carrying the active substance can move more freely through the nasal gel when the gel is less viscous.

Similarly, the rate of diffusion of an active substance through the nasal gel itself can be increased by decreasing the viscosity of the nasal gel or by using a liposome or other chemical component which facilitates the diffusion of an active substance through the nasal gel either by carrying the active substance or by interacting with the nasal gel to facilitate the passage and diffusion of the active substance through the nasal gel. The diffusion rate of an active substance through the nasal gel itself is important when the concentration of the active substance in the gel becomes less near or at the gel—nasal membrane interface. When the concentration in the gel of the active substance near or at the gel-nasal membrane interface becomes less than the concentration of the active substance in the remainder of the gel, it is desirable that the active substance readily diffuse through the gel to replenish the concentration of the active substance at or near the gel—nasal membrane interface. The concentration of the active substance at or near the gel—nasal membrane interface becomes less when the active substance is absorbed from the gel into the nasal membrane. Liposomes or other chemical components can be included in nasal gel at concentrations in the range of 0.000001% to 5.0% by weight.

The rate of diffusion of an active substance through mucous in the nasal passage can be increased by using in the gel composition an agent like zinc or salt which facilitate the breakup and drying of mucous in the nose or by using in the gel composition a component which actually facilitates travel of an active substance through mucous. Mucous is a protein and has different properties than the nasal epithelial membrane. Agents like zinc or salt can be included in the nasal gel in concentrations in the range of 0.000001% to 5% by weight.

Another method of facilitating the diffusion of an active substance into the nasal membrane is to spread the nasal gel over a larger surface area of the nasal membrane. One way this is facilitated is by enhancing the action of the cilia which tend to beat or carry mucous or foreign substances in the nose toward the back of the throat. Chemical components like lysozyme can be included in the nasal gel in concentrations in the range of 0.00001% to 5.0% by weight to increase the action of cilia and to therefore increase the rate at which the gel composition is, after being inserted in a patient's nose, carried rearwardly from the nose down through the nasal passage into the back of the patient's throat. Increasing the action of the cilia functions to increase the rate at which the nasal gel coats a greater surface area in the nasal passage. As used herein, the nasal passage begins inside the nose at a point about one-quarter of an inch to one-half from the opening in each nostril and extends to the back of a patient's throat. The nasal passage includes portions of each nostril of a patient's nose.

Absorption of an active substance in the gel of the invention in the lungs or nasal membrane can be facilitated by sublimation. For example, camphor or iodine can be admixed with the nasal gel of the invention at some time prior to inserting the gel in a patient's nose. The concentration of a sublimating active substance can vary as desired, but typically is in the range of 0.00001% to 5.0% by weight.

In the nasal gel, it is sometime important to keep an active substance like zinc in its ionized state. One way of increasing the likelihood that an active substance will remain in its ionized state is by increasing the viscosity of the nasal gel.

Still a further way of increasing the likelihood that an active substance will remain in its ionized state is by using a thickener which will not bind with the active substance when the active substance in an ionize state. For example, carbopol does bind with zinc and generally is therefore not a preferred thickener in gel compositions in which it is desired to maintain zinc in its ionized state. Most thickeners do not bind with zinc ions. Ascorbic acid also binds with zinc. Therefore ascorbic acid ordinarily is not utilized in combination with a gel composition including ionic zinc as an active substance. Glycerine functions to help maintain zinc and other components in their ionic state.

When the nasal gel includes zinc ions and is being utilized to treat rhinovirus, it is important to use the gel in both nostrils of the patient's nose. In other circumstances, for example delivering a vitamin into the patient's bloodstream, it is not necessary that the gel be placed in both nostrils. Use of only one nostril may be sufficient.

It may be desirable to utilize a nasal gel composition which thickens when placed in the nostril of a patient. Utilizing a component which is temperature sensitive and thickens due to the increased temperature in a patient's nose is one avenue of producing an increased viscosity when the nasal gel is applied in the patient's nose. Another avenue is to admix two or more components just prior to applying the nasal gel in the patient's nose. The two components produce a composition having a viscosity greater than either component separately.

The nasal gel of the invention can be packaged in a capsule or other container which dissolves on being inserted in the nose. When the container dissolves, the gel contacts the nasal membrane. The capsule can be fabricated from gelatin, from a soft pliable paper-like water soluble material, or from any other desired material that dissolves or disintegrates or otherwise degrades when placed in the nasal cavity.

EXAMPLE 14

One liter of a gel composition is prepared by mixing together purified water, glycerin, carbopol, liposomes, and insulin. The gel includes:

| Component | Weight Percent |
| --- | --- |
| PURIFIED WATER | 96.5 |
| GLYCERIN U.S.P. | 2.0 |
| CARBOPOL 940 nf | 0.5 |
| INSULIN | 0.5 |
| LIPOSOMES (carrier for insulin) | 0.5 |

EXAMPLE 15

Two hundred microliters of the gel of Example 14 is placed in one nasal passage of a healthy thirty-nine year old male Caucasian patient. Two hundred microliters of the zinc gel of Example 1 is then placed in the other nasal passage of the patient. Consequently, a total of 400 microliters of the gel is placed in the patient's nose. A first portion of the gel contacts at least a portion of the nasal epithelial membrane. A second portion of the gel contacts at least a portion of the mucous in the patient's nose. A third portion of the gel contacts at least cilia in the patient's nose. The gel remains in contact with at least a portion of the nasal epithelial membrane, the cilia, or mucous on the membrane. After four hours the zinc gel has completely dissipated.

EXAMPLE 16

One liter of a gel composition is prepared by mixing together purified water, oil, glycerin, carbopol, liposomes, and vitamin A. The gel includes:

| Component | Weight Percent |
|---|---|
| PURIFIED WATER | 86.5 |
| OMEGA 6 (MONOSATURATED OIL) | 10.0 |
| GLYCERIN U.S.P. | 2.0 |
| CARBOPOL 940 nf | 0.5 |
| VITAMIN A | 0.5 |
| LIPOSOMES (carrier for vitamin A) | 0.5 |

EXAMPLE 17

Three hundred microliters of the gel of Example 16 is placed in one nasal passage of a healthy twenty-eight year old female Chinese patient. Consequently, a total of 300 microliters of the gel is placed in the patient's nose. A first portion of the gel contacts at least a portion of the nasal epithelial membrane. A second portion of the gel contacts at least a portion of the mucous in the patient's nose. A third portion of the gel contacts at least cilia in the patient's nose. The gel remains in contact with at least a portion of the nasal epithelial membrane, the cilia, or mucous on the membrane. After four hours the zinc gel has completely dissipated.

EXAMPLE 18

One liter of a gel composition is prepared by mixing together purified water, alcohol, glycerin, carbopol, and nicotine. The gel includes:

| Component | Weight Percent |
|---|---|
| PURIFIED WATER | 87.25 |
| ALCOHOL | 10.0 |
| GLYCERIN U.S.P. | 2.0 |
| CARBOPOL 940 nf | 0.5 |
| NICOTINE | 0.25 |

EXAMPLE 19

One hundred and fifty microliters of the gel of Example 18 is placed in one nasal passage of a healthy fifty year old female African American patient. Consequently, a total of 150 microliters of the gel is placed in the patient's nose. A first portion of the gel contacts at least a portion of the nasal epithelial membrane. A second portion of the gel contacts at least a portion of the mucous in the patient's nose. A third portion of the gel contacts at least cilia in the patient's nose. The gel remains in contact with at least a portion of the nasal epithelial membrane, the cilia, or mucous on the membrane. After three hours the zinc gel has completely dissipated.

EXAMPLE 20

One liter of a gel composition is prepared by mixing together purified water, glycerin, carbopol, zinc gluconate, and SOD. The gel composition includes:

| Component | Weight Percent | |
|---|---|---|
| PURIFIED WATER | 94.75 | |
| GLYCERIN U.S.P. | 2.0 | |
| CARBOPOL 940 nf | 0.5 | |
| ZINC GLUCONATE (source of ionic zinc) | 2.25 | (50 millimolar concentration) * |
| SOD (antioxidant) | 0.5 | |

* The molecular weight of zinc gluconate, about 450 g/mole, multiplied times 0.05 moles per liter of zinc gluconate gives a weight of about 22.5 grams per liter of the gel composition.

The SOD antioxidant functions to protect the nasal epithelial membrane from damage due to the high concentrations of zinc ion in the nasal gel.

EXAMPLE 21

Examples 2 to 7 are repeated utilizing the gel composition of Example 20 in place of the gel composition of Example 1. Similar results are obtained.

EXAMPLE 22

Example 7 is repeated except the patient has a layer of mucous about one-sixteenth of an inch thick covering the nasal mucosa. Similar results are obtained.

EXAMPLE 23

Example 22 is repeated except that the gel composition of Example 1 also includes 1.0% by weight NaCl and that the weight percent of the purified water in the gel composition is 96% instead of 97%. The weight percent of glycerin, carbopol, and zinc gluconate in the gel composition of Example 1 remain the same. The salt is included in the gel composition in order to facilitate the diffusion of zinc through the layer of mucous.

The results obtained in this Example 23 are similar to those in Example 22, except that zinc concentration in the nasal mucosa increases more rapidly in Example 23 because the salt facilitates drying and dissipation of the layer of mucous.

EXAMPLE 24

Example 7 is repeated except that the gel composition of Example 1 is inserted in the nasal passage in the nose and, instead of measuring the concentration of zinc in the nasal mucosa just prior to administration of the zinc gel, ten minutes after administration of the zinc gel, one-half hour after administration of the zinc gel, etc., the distance the zinc gel has been carried back into the nasal cavity by cilia in the nasal cavity after ten minutes, one-half hour, etc. is measured.

EXAMPLE 25

Example 24 is repeated except that the gel composition of Example 1 also includes 0.5% by weight lysozyme and that the weight percent of the purified water is 96.5% instead of 97%. The weight percent of glycerin, carbopol, and zinc gluconate in the gel composition of Example 1 remain the same. The lysozyme included in the gel composition increases the activity of cilia in the nose and, as a result, increases the rate at which cilia carry zinc gel from inside the nose back through the nasal cavity toward the back of the patient's throat. The results obtained in Example 25 are similar to those obtained in Example 24, except in Example 25 the cilia more rapidly carry zinc gel toward the back of the patient's throat.

EXAMPLE 26

The gel composition of Example 1 is placed against a surface which removes zinc from the gel at the gel—surface interface at a selected rate. The rate of diffusion of zinc from a selected point (the point being a selected distance from the interface) to the interface is measured.

EXAMPLE 27

Example 26 is repeated, except the viscosity of the gel composition of Example 1 is reduced by reducing the concentration of carbopol to 0.25 weight percent and reciprocally increasing the concentration of purified water to 97.25%. The concentration of glycerin and zinc gluconate remain the same. The results obtained are similar, except that the rate of diffusion of zinc ions is greater in this Example 27 than in Example 26 because of the reduced viscosity of the gel composition.

EXAMPLE 28

Example 15 is repeated, except that concentration of insulin in the nasal membrane is measured at 10, 20 and 30 minutes.

EXAMPLE 29

Example 28 is repeated, except that the liposomes are removed from the gel composition of Example 14 and the concentration of purified water is reciprocally increased to 97% by weight. The liposomes are permeation enhancers which are added to enhance the ability of the insulin to permeate the nasal epithelial membrane. The concentration of glycerin, carbopol, and insulin in the gel composition of Example 14 remain the same. The results obtained in this Example 29 are different from those obtained in Example 28, because the concentration of insulin in the nasal mucosa rise more slowly because the liposome permeation enhancers are no longer present in the gel composition.

Having described our invention in such terms as to enable those skilled in the art to understand and practice it, and having identified the presently preferred embodiments thereof,

We claim:

1. A method of delivering minor effective amounts of an active substance into the blood, comprising the steps of
   (a) providing a viscous gel delivery composition including
      (i) 75% to 99.999% by weight of at least one carrier, and
      (ii) a minor effective amount of the active substance comprising zinc,
   (b) applying said delivery composition in the nasal cavity, said nasal cavity including mucous, cilia and a nasal membrane, said delivery composition being applied such that a first portion of said composition directly contacts at least the nasal membrane, a second portion of said composition directly contacts at least mucous in the nasal cavity, and at least a third portion of said composition directly contacts at least cilia in the nasal cavity; and,
   (c) maintaining said first portion of said delivery composition in contact with the nasal membrane for at least ten minutes.

2. The method of claim 1, wherein the step of providing a viscous delivery composition further comprises providing zinc ions.

3. The method of claim 1, wherein the step of providing a viscous delivery composition further comprises providing about 1.5 wt% of zinc gluconate.

4. The method of claim 1, wherein the step of providing a viscous delivery composition further comprises providing about 0.000001 wt% to about 5.0 wt% thickener.

5. The method of claim 4, wherein the step of providing a thickener includes providing a carbohydrate.

6. A method of delivering a minor effective amount of an active substance to the blood and of reducing the time required for the active substance to pass through membrane into the blood by increasing the surface area over which the active substance contacts of the body, comprising the steps of
   (a) providing a viscous gel delivery composition including
      (i) 75% to 99.999% by weight of at least one carrier, and
      (ii) a minor effective amount of the active substance comprising zinc,
   (b) applying said delivery composition in the nasal cavity,
      (i) the nasal cavity including a nasal membrane, cilia and mucous,
      (ii) a first portion of said composition directly contacting at least said nasal membrane, a second portion of said composition directly contacting at least said mucous in the nasal cavity, and at least a third portion of said composition directly contacting at least said cilia in the nasal cavity; and,
   (c) increasing the activity of the cilia in the nasal cavity.

* * * * *